United States Patent
Ivancevich et al.

(10) Patent No.: US 9,332,963 B2
(45) Date of Patent: May 10, 2016

(54) SWEPT FOCUS FOR ACOUSTIC RADIATION FORCE IMPULSE

(71) Applicants: Nikolas M. Ivancevich, Seattle, WA (US); Xiaozheng Zeng, Sammamish, WA (US); Liexiang Fan, Sammamish, WA (US)

(72) Inventors: Nikolas M. Ivancevich, Seattle, WA (US); Xiaozheng Zeng, Sammamish, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 107 days.

(21) Appl. No.: 14/160,440

(22) Filed: Jan. 21, 2014

(65) Prior Publication Data

US 2015/0201905 A1 Jul. 23, 2015

(51) Int. Cl.
| | |
|---|---|
| *A61B 6/00* | (2006.01) |
| *A61B 8/08* | (2006.01) |
| *A61B 8/00* | (2006.01) |
| *G01S 7/52* | (2006.01) |

(52) U.S. Cl.
CPC . *A61B 8/485* (2013.01); *A61B 8/08* (2013.01); *A61B 8/4466* (2013.01); *A61B 8/4483* (2013.01); *A61B 8/461* (2013.01); *A61B 8/5207* (2013.01); *G01S 7/52042* (2013.01)

(58) Field of Classification Search
CPC .......................... A61B 8/485; A61N 2007/027
USPC ............................................................. 600/438
See application file for complete search history.

(56) References Cited

U.S. PATENT DOCUMENTS

| | | | |
|---|---|---|---|
| 5,608,690 | A | 3/1997 | Hossack et al. |
| 7,252,004 | B2 | 8/2007 | Fink et al. |
| 2010/0016718 | A1* | 1/2010 | Fan et al. ............. 600/438 |
| 2011/0178407 | A1* | 7/2011 | Lu et al. ............... 600/459 |
| 2011/0184287 | A1 | 7/2011 | McAleavey |
| 2012/0215101 | A1 | 8/2012 | Maleke et al. |

FOREIGN PATENT DOCUMENTS

| | | |
|---|---|---|
| EP | 2 294 983 | 3/2011 |
| WO | WO 2011/132014 A1 | 10/2011 |
| WO | WO 2012/080913 | 6/2012 |
| WO | WO 2013/015001 | 1/2013 |

OTHER PUBLICATIONS

PCT Search Report and Written Opinion dated Apr. 16, 2015 in counterpart PCT application No. PCT/US2015/012227, international filing date Jan. 21, 2015, 12 pages total.

* cited by examiner

*Primary Examiner* — Joel F Brutus (57) ABSTRACT

Acoustic radiation force impulse (ARFI) scanning uses a swept focus in transmit. Using a changing delay or phase profile across the array during the generation of the ARFI pulse, a time varying focus is provided for the ARFI beam. This time varying focus may be used to extend the focus in depth, azimuth, and/or elevation. Less repetition may be needed to measure tissue characteristics from displacements due to the multi or continuous change in foci within a given ARFI transmit beam.

20 Claims, 5 Drawing Sheets

FIG. 11

SWEPT FOCUS FOR ACOUSTIC RADIATION FORCE IMPULSE

BACKGROUND

The present embodiments relate to acoustic radiation force impulse (ARFI) imaging. By transmitting an ARFI pushing pulse, ultrasound may be used to displace tissue directly or through generation of a shear or longitudinal wave. The displacement resulting from the pushing pulse may be measured using further ultrasound scanning. Elasticity, shear, or other types of parametric imaging measure tissue characteristics based on the displacement caused by the ARFI pulse. Tissue with different characteristics responds to displacement differently.

The ARFI pulse is transmitted as a focused beam. The beam has an hour-glass shape with the narrow portion being at the single focus. The beam shape causes a non-uniform response, resulting in less signal-to-noise ratio for displacements measured in some locations. As a result, a limit range of locations are available for measuring tissue characteristics for a given ARFI pulse. To measure over a range of depths, a rapid sequence of separate ARFI pulses focused at different depths is generated. Laterally, the narrow beam width at the focal point limits the lateral extent to which measurements may be applied. ARFI pulses are repeated to measure displacement at different laterally spaced locations. However, the repetition of ARFI pulses may cause undesired transducer heating and introduces delays in scanning.

BRIEF SUMMARY

By way of introduction, the preferred embodiments described below include methods, instructions, and systems for swept focus in acoustic radiation force impulse (ARFI) scanning. Using a changing delay or phase profile across the array during the generation of the ARFI pulse, a time varying focus is provided for the ARFI beam. This time varying focus may be used to extend the focus in depth, azimuth, and/or elevation. Less repetition may be needed to measure tissue characteristics from displacements due to the broader extent of focused ultrasound within a given ARFI transmit beam.

In a first aspect, a method is provided for swept focus in acoustic radiation force impulse scanning. An ultrasound transducer transmits a transmit beam with a time varying focal position as an acoustic radiation force impulse. Displacements of tissue at different depths from the ultrasound transducer are tracked. The displacements are responsive to the acoustic radiation force impulse. An image is generated. The image is a function of the displacement of the tissue at the different depths.

In a second aspect, a non-transitory computer readable storage medium has stored therein data representing instructions executable by a programmed processor for swept focus in acoustic radiation force impulse scanning. The storage medium includes instructions for altering a phase profile across an array of transducers over a time period, generating continuous transmit waveforms over the time period with the altering phase profile, and transmitting a beam of acoustic energy as an acoustic radiation force impulse from the array with the continuous transmit waveforms over the time period, the beam having a line focus in response to the altering phase profile.

In a third aspect, a system is provided for swept focus in acoustic radiation force impulse scanning. A transmit beamformer is configured to generate waveforms for an acoustic radiation force impulse pulse with a time varying focal point in elevation, azimuth, range, or combinations thereof. An ultrasound transducer connects with the transmit beamformer such that the ultrasound transducer transmits the acoustic radiation force impulse pulse in a patient in response to the waveforms. A receive beamformer is operable to output data representing spatial locations as a function of received acoustic signals. A processor is configured to estimate displacement in the patient over time as a function of the output data. A display is operable to display an image where the image being a function of the displacement.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An acoustic radiation force impulse (ARFI) with a longer depth of field or wider push than currently achievable using a single focus is provided. An ultrasound transducer creates an ARFI pulse with a time-varying focal point in elevation, azimuth or range during a single ARFI transmission. Additionally, the amplitude may be modulated during the focal sweep in order to produce a more uniform push. If used to sweep the beam in range, a more uniform image along depth may result. Fewer focal zones are needed, reducing scan time and acoustic output. If used to sweep the beam in azimuth or elevation, a push that encompasses more parallel receive beams may result, decreasing scan time and acoustic output.

Figure 1:
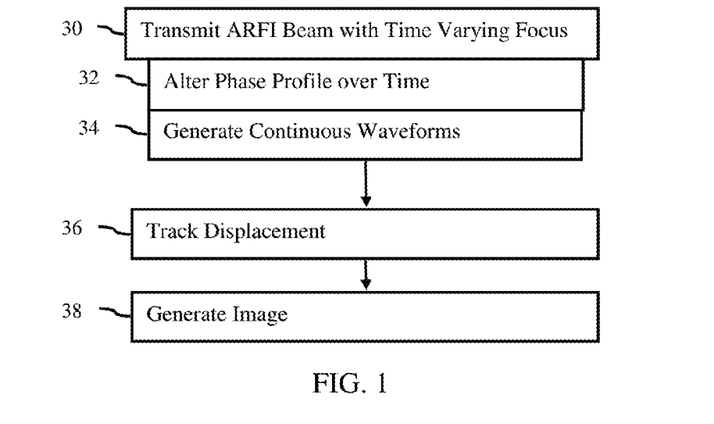
FIG. 1 is a flow chart diagram of one embodiment of a method for swept focus in acoustic radiation force impulse scanning.

FIG. 1 shows a method for swept focus in acoustic radiation force impulse scanning. An ultrasound transmission is used to generate tissue displacement. By sweeping the focus of a given ARFI pulse, a single transmit beam with a line, extended or multiple foci is created. The ARFI beam may apply force more uniformly to the tissue, allowing for greater range of depths and/or for a greater lateral extent over which displacement may be detected.

Figure 12:
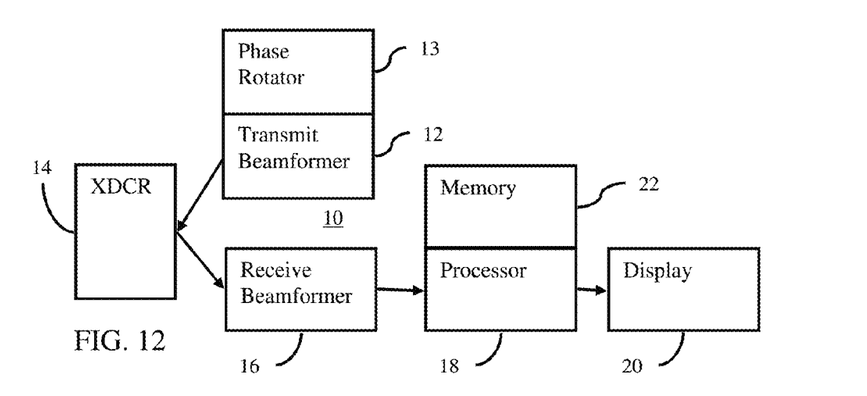
FIG. 12 is one embodiment of a system for swept focus in acoustic radiation force impulse scanning.

The method is implemented by the system of FIG. 12 or a different system. Additional, different, or fewer acts may be provided. For example, the method is performed without generating an image in act 38. As another example, act 30 is performed without one or more of acts 32 or 34. In yet another example, acts for estimating tissue characteristics or properties from the displacements are provided. The acts are performed in the order described or shown, but may be performed in other orders.

In act 30, an acoustic radiation force impulse (ARFI) beam is transmitted. The beam has a time varying focus. An array of elements in an ultrasound transducer transmits the ARFI beam converted from electrical waveforms. The acoustic energy with the time varying focus is transmitted to the tissue in a patient. The excitation is focused at a plurality of locations to allow detecting of the resulting shear wave or waves over a broader range of depths and/or lateral (e.g., azimuth and/or elevation) positions in tissue of interest (e.g., tissue region surrounding and/or including a possible tumor).

The acoustic waveform is transmitted for generating a shear, longitudinal, or other wave as stress to displace tissue. The excitation is an ultrasound pushing pulse. The acoustic energy is focused to apply sufficient energy to cause generation of one or more waves travelling through the tissue from the focal locations. The acoustic waveform may itself displace the tissue.

The shear wave or waves are generated at the focal region and propagate laterally, axially, and/or in other directions from the focal region. The waves may travel in multiple directions. The waves reduce in amplitude as the waves travel through the tissue. An extended or swept focal region may allow for sampling displacements in a broader region of tissue despite the attenuation.

To generate the wave, high amplitude or power excitations are desired. For example, the excitation has a mechanical index of close to but not exceeding 1.9 at any of the focal locations and/or in the field of view. To be conservative and account for probe variation, a mechanical index of 1.7 or other level may be used as the upper limit Greater (e.g., MI exceeding 1.9) or lesser powers may be used.

The focus for the generating the wave or waves is swept. To sweep the focus, the location of the focus is changed over time. A given ARFI transmission occurs over a time period. One or more elements begin outputting acoustic energy first and others join at different times based on relative delay or phasing. The waveforms for each element continue, with some ending before others end. This time period is for one beam or pushing pulse transmission and extends from the time at which the array starts generating acoustic energy and ends at the time at which the array then ceases generating acoustic energy. The sweep in focus occurs during the time period for generating a given transmit beam.

The excitation is focused using a phased array with or without a mechanical focus. A mechanical focus may be provided for a given direction, such as an elevation focus. Azimuth and/or axial mechanical focus may be provided. In at least one direction and possibly all three (e.g., axial, azimuth, and elevation), the array of elements are electronically focused. The electronic focus allows variation of the focus during the time period.

To sweep the focus, the phase profile, delay profile or both are altered over the time period in act 32. Other approaches for sweeping the focus may be used. For transmitting a beam with a single focal point, the phase profile is constant in time. During the time period, the same relative phase between the waveforms of the different elements is used. For a swept focus, the phase profile across the array varies during the time period. The amount of relative phase difference between two or more waveforms of elements of the array changes. The phase is changed differently for some waveforms and corresponding elements than for others. To focus at a different location, a different phase profile is used. The phase profile is different by having different relative delays between the elements. In sweeping the focus to move the focal location, the different delay profiles are implemented. At different times in the time period, different relative phasing is applied.

As a given waveform for a given element is generated, the phase relative to other waveforms changes. A phase rotator or delay adjustment may be used. Alternatively, the waveform is generated with the variance in relative phase or delay. The changes in relative phases or delays across the array cause parts of the respective waveforms to be focused at different locations. The focus for the transmit beam varies during the time period for which the beam is generated.

Any change function may be used for the phase or delay. In one embodiment, the phase profiles constantly change over time. The change occurs every N clock cycles of the transmit beamformer wherein N is an integer. N may be 1 for constant change. For less frequent change, N may be a greater number. In other approaches, constant change is provided with N greater than one but sufficient to cause less than 2 dB down from the peak along a continuous focal region.

Depending on the focal locations, the phase for one or more waveforms and/or elements may not change at all or not change for a number of clock cycles. For example, the phase applied to the waveform for a center element of an array where the focus is swept axially along a normal to the array may be the same for the entire time period. Phases for the waveforms of elements at the ends of the aperture may have the greatest variance and rates of change. For the array, the one or more phase terms are constantly changing.

The phase change may be implemented using a phase rotator. In one embodiment, the phase is controlled using different phase terms, such as constant phase, linear phase, and quadratic phase terms. Additional, different, or fewer phase terms may be used. To maintain the same relative phase for a single focal point, the phase terms are constant in time. To sweep the focus, one, more, or all of the phase terms may vary over time. The phase terms for a swept focus are channel and time dependent rather than just being channel dependent for a single focus location.

The rate of change in the phase profile or phase for given elements is constant. The rate may be different for different elements depending on the steering angle and the element position within the aperture. In other embodiments, the rate of change in phase varies. For example, the rate of change may be slower for some range of focal locations to increase the dwell time or amount of acoustic energy transmitted while focused in that region or range of locations. The rate of change may be zero for some focal locations, at least for a part of the time period. The focal position may vary over time with discrete steps in position rather than constant variance.

In one embodiment, the delay on a channel is expressed as:

$$\Delta t_i = \frac{\sqrt{\text{focus}^2 + x_i^2} - \text{focus}}{c}$$

where c is the speed of sound, distance from center of the array and i is the element number. The focal point is a function of time, represented as F(t). The voltage for the elements is:

$$V(t,x) = A_0 \sin(2\pi f(t + \Delta t_i)),$$

where A is the amplitude, f is the frequency, and $\Delta t_i$ is a function of time and channel such that:

$$\Delta t(t, x_i) = \frac{\sqrt{F(t)^2 + x_i^2} - F(t)}{c}.$$

Then:

$$V(t,x) = A_0 \sin(2\pi f(t + \Delta t(t,x))).$$

For a single focus, $\Delta t$ is constant and is applied as a gross delay. The element voltage for a time varying focus is written as:

$$V(t, x) = A_0 \sin\left(2\pi f\left(t + \left(\frac{\sqrt{F(t)^2 + x_i^2} - F(t)}{c}\right)\right)\right) =$$

$$A_0 \sin\left(2\pi f\left(t + F(t)\frac{\sqrt{1 + \frac{x^2}{F(t)^2}}}{c} - \frac{F(t)}{c}\right)\right).$$

If $$\frac{x^2}{F(t)^2}$$

is much less than 1, then the Taylor series expansion may be used. For $F\# = z/D$ between 2 and 4, if $$\frac{z}{D} = 4 = \frac{F(t)}{2 x_{max}}$$

such that $$\frac{x^2}{F(t)^2} = \frac{1}{64}.$$

$$\text{If } \frac{z}{D} = 2, \text{ then } \frac{x^2}{F(t)^2} = \frac{1}{16}.$$

Higher F#s provide better $$\frac{x^2}{F(t)^2}.$$

$V(t, x)$ may be written as:

$$A_0 \sin\left(2\pi f\left(t + \left(\frac{1}{2c}\right)\left(\frac{x^2}{F(t)^2}\right)\right)\right).$$

$$\text{If } F(t) = \frac{1}{at^2 + 2b + c},$$

then:

$$V(t, x) = A_0 \sin\left(2\pi f\left(t + \left(\frac{1}{2}\right)\left(\frac{x^2}{c}\right)(at^2 + bt + c)\right)\right) =$$

$$A_0 \sin\left(\left(2\pi f\left(\frac{ax^2 t^2}{c}\right)\right) + 2\pi f\left(1 + \left(\frac{\frac{1}{2}x^2 b}{c}\right)\right)t + \left(\frac{2\pi fc}{2}\right)x^2\right).$$

This has quadratic, linear, and constant terms for the phase.

A single transmit beam is transmitted with the time varying focal position. In other embodiments, a given transmit event may form more than one beam (e.g., simultaneous multi-beam). One, some, or all of the transmit beams have time varying foci. Whether transmitting a single beam or multiple beams during a given transmit event, the transmission event occurs over a time period of uninterrupted generation of acoustic energy by the array. At least one element is generating acoustic energy at any point during the time period. Subsequent beams may be formed in a non-continuous manner, such as by having a period of one or more waveform cycles without any of the elements of the array generating acoustic energy. Non-continuously formed beams may be based on most of the elements or other number of elements not generating acoustic energy.

During the time period, the waveforms applied to the elements are generated in act 34 as continuous waveforms. The waveforms vary, such as being square wave, sinusoidal waves, or other unipolar or bipolar alternating waveforms. The waveform does not have any extended periods of zero output other than to begin and end the waveform. An extended period is one or more cycles. There may be part of each cycle at zero, such as for a unipolar square wave, but another part of the cycle has non-zero (positive or negative) output. The continuous waveform is subjected to or generated with the altering phase profile, so includes phase adjustments as applied to the element.

The ARFI beam is transmitted with waveforms having any number of cycles. In one embodiment, one, most, or all of the waveforms for a transmit event have 100-2,000 cycles. The number of cycles is tens, hundreds, thousands, or more for the continuous transmit waveforms applied to the elements of the array for the ARFI beam. Unlike imaging pulses that are 1-5 cycles, the ARFI pushing pulse has a greater number of cycles to generate sufficient stress to cause the wave for displacing tissue with an amplitude sufficient to detect.

The length of the transmission in combination with the amplitude provides acoustic power to the tissue. This power may cause a rise in temperature in the tissue. Transmitting along the same or adjacent scan lines may cause the tissue to increase in temperature over time. Biological effects may include hyperthermia at tissue temperature of about 41-45° C., protein denaturation at temperatures above 43-45° C., and tissue necrosis at temperatures above 50° C. Tissue stiffness may be affected even at temperatures below 43-45° C. At temperatures above 43-45° C., increases in viscosity and/or stiffness may occur. At temperatures above 50° C., the tissue may have a high stiffness and/or high attenuation. Biological effects are limited by preventing a temperature increase of over 2 degrees Celsius. Alternatively, the transmissions may cause biological effects. By using a swept focus, a broader region is subjected to tissue displacement for each ARFI beam, resulting in less temperature rise for the transducer and/or the tissue to scan a given region of interest.

A pushing pulse beam of acoustic energy is transmitted. ARFI is transmitted from the array by application of the continuous transmit waveforms to the elements of the array over the time period. The pushing pulse has a time varying focus, such as a line focus. The line is straight or curved. The line is continuous, but may be for multiple discrete regions (not continuous). The focus changes position over the time period during which the transmit beam is generated.

Figure 2:
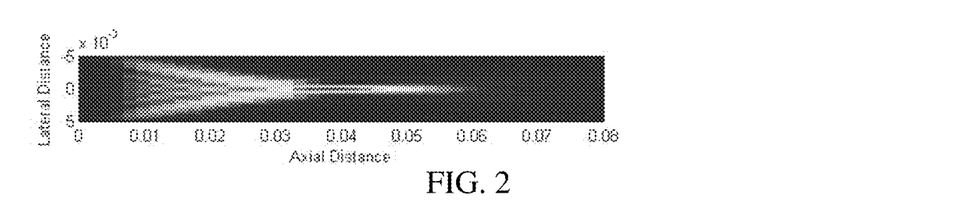
FIGS. 2 and 3 are example azimuth and elevation beam simulations of an ARFI beam with a single focus.
Figure 3:
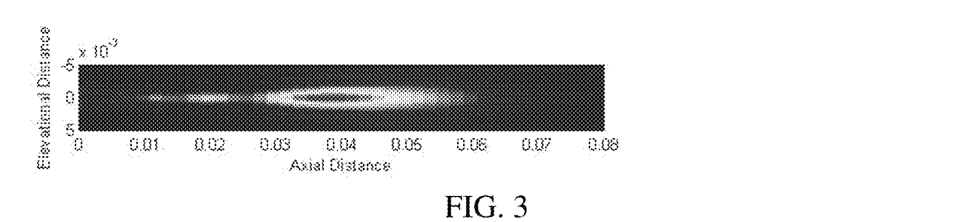
Figure 4:
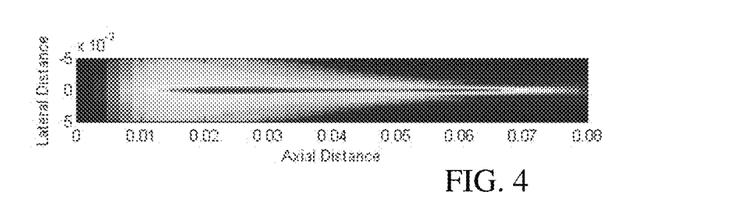
FIGS. 4 and 5 are example azimuth and elevation beam simulations of an ARFI beam with an axially swept focus.
Figure 5:
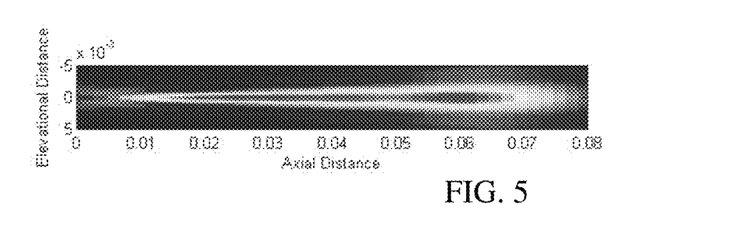
Figure 6:
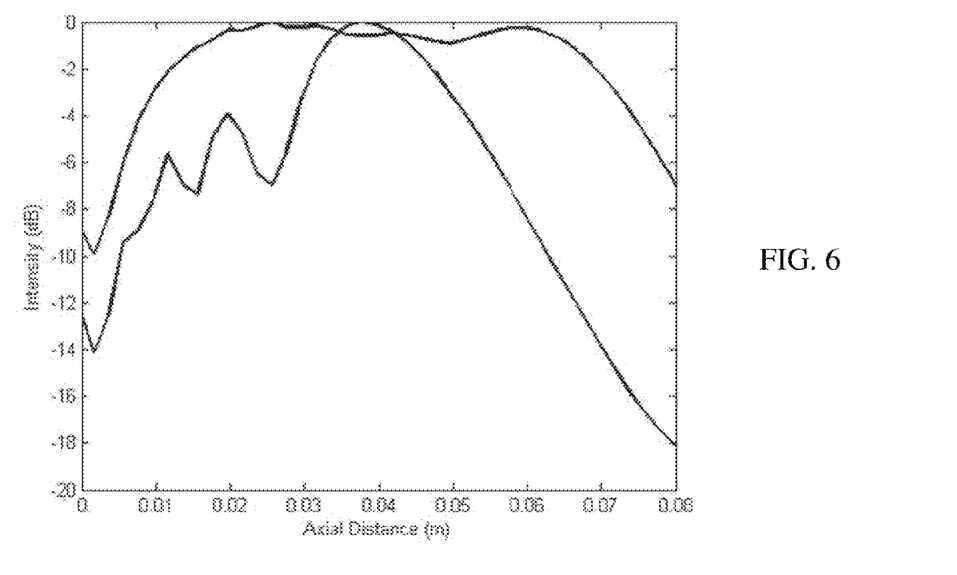
FIG. 6 illustrates an example axial beam plot for the ARFI beam simulated in FIGS. 4 and 5.

The focal position varies axially, laterally or axially and laterally. FIGS. 2-6 demonstrate extending the focus over the depth of field or axially. The time varying focal position varies by axial position. FIGS. 2 and 3 are simulations of an ARFI beam in azimuth and elevation, respectively, with a single focus at 4 cm. The focal region appears extended, but only over a 1 cm range, due to imperfect focus of an array. FIGS. 4 and 5 are simulations of an ARFI beam in azimuth and elevation, respectively, with continuously swept focal positions from 6 cm to 2 cm. The axial extent of the focal region is a line with much greater range than the single focus. FIG. 6 is an axial beam plot showing the single focus with a peak of 4 cm but little axial range and the swept focus with less than 2 dB drop from the peak over a 4 cm range (e.g., from 2 cm to 6 cm). Swept focus with more or less drop in the focal range may be provided.

Figure 7:
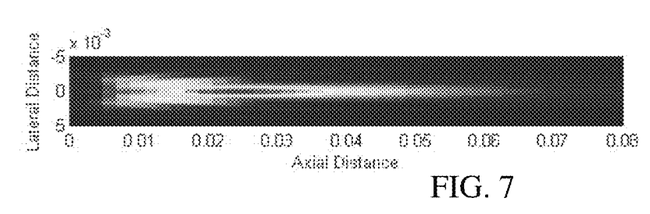
FIGS. 7 and 8 are example azimuth and elevation beam simulations of an ARFI beam with a single focus.
Figure 8:
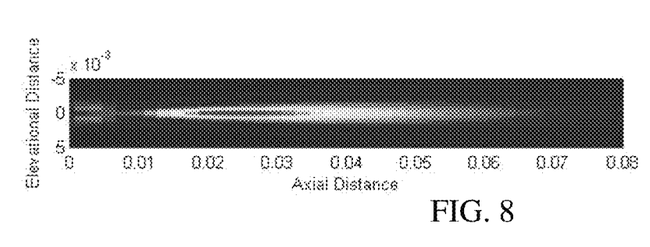
Figure 9:
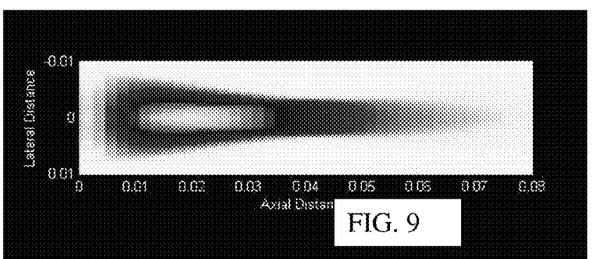
FIGS. 9 and 10 are example azimuth and elevation beam simulations of an ARFI beam with a laterally swept focus.
Figure 10:
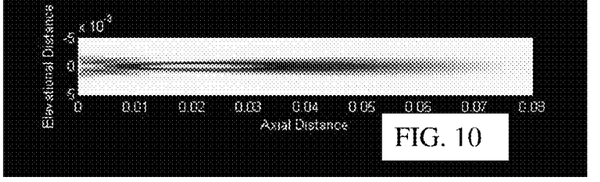
Figure 11:
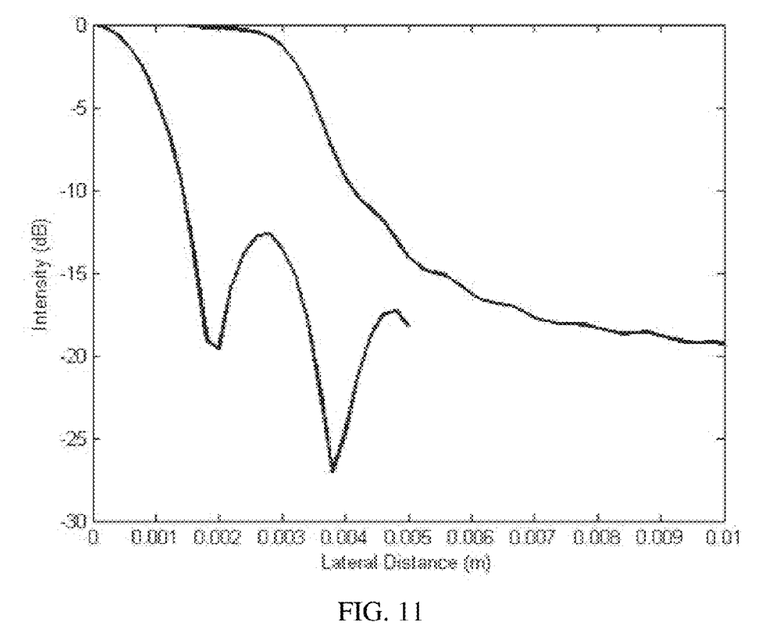
FIG. 11 illustrates an example lateral beam plot for the ARFI beam simulated in FIGS. 9 and 10.

FIGS. 7-11 demonstrate extending the focus laterally or by lateral position. The time varying focal position varies laterally. Azimuth is represented, but extending the focus over elevation as the lateral change may be used. FIGS. 7 and 8 are simulations of an ARFI beam in azimuth and elevation, respectively, with a single focus at 2.5 cm. The focal region has azimuth and elevation width, but is relatively narrow. FIGS. 9 and 10 are simulations of an ARFI beam in azimuth and elevation, respectively, with continuously swept focal positions in azimuth from −3 mm to 3 mm. The azimuth extent of the focal region is spread along the azimuth line with a much greater lateral extent than the single focus. In elevation and depth, the focal region of the swept focus transmit beam has a similar extent as the single focus transmit beam. FIG. 11 is an azimuth beam plot showing the single focus with a 1-2 mm azimuth beam width and the swept focus with a 6-7 mm azimuth beam width. Beam width is measured from −2 dB, but may be at other intensities (e.g., −5 dB). Swept focus with more or less drop in the focal range may be provided.

The ARFI beam is generated with constant amplitude modulation. In an alternative embodiment, the amplitude of the transmit beam is varied over time with the time varying focal position. For example, greater amplitudes are provided for focal locations at deeper depths. The amplitudes of the electrical waveforms applied to the elements to generate the beam vary as a function of time over the time period. The variation rate is constant, but may vary.

The ARFI beam is generated with a constant aperture. For example, all 128 or 256 elements are used for each focal position. In other embodiments, the aperture size (e.g., channel mask) varies with the time varying focal position. To maintain constant F#, the size of the aperture may increase or decrease based on focal position. Some elements are used for some but not all focal depths of the time varying focus. The aperture may be smaller (e.g., fewer number of elements) for closer focal positions and larger for deeper focal positions.

Referring again to FIG. 1, displacements are tracked in act 36. The tissue response is a function of the wave created by the ARFI beam and the tissue characteristics. The displacement of the tissue over time may be expressed as a convolution of the waveform and the tissue characteristics or response. The tissue response reflects viscoelastic properties of the tissue.

One or more viscoelastic properties are measured from displacement caused by the transmit beam with the time varying focal positions generated in act 30. In order to measure the viscoelastic properties, the displacement of the tissue over time in response to the pushing pulse is measured. The displacement of the tissue caused by the created wave or the ARFI pulse itself is determined over time. As the wave passes a given location, the tissue displaces by an amount or distance that increases to a peak amount and then decreases as the tissue returns to rest.

In act 36, the displacement is calculated as a function of time. The tissue is scanned multiple times to determine the displacement, such as scanning a region at least three times to determine displacement at two different times. The tissue is scanned using any imaging modality capable of scanning for displacement during the tissue's response to the pushing waveform, such as during or after application of the ARFI pushing pulse. The scan occurs over a range of times where the desired waveform (e.g., shear wave) would be passing through the tissue.

For ultrasound scanning, the wave is detected at locations adjacent to and/or spaced from the focal region for the ARFI pushing pulse. To detect the displacement, ultrasound energy is transmitted to the tissue undergoing displacement, and reflections of the energy are received. To detect tissue response to waves in a region of interest, transmissions are made to the region, and detection is performed in the region. These other transmissions are for detecting the waves or displacement rather than causing the wave or displacement. The transmissions for detection may have lower power and/or short pulses (e.g., 1-5 carrier cycles) and use the same or different scan line as the ARFI beam. The transmissions for detection may have a wider beam profile along at least one dimension, such as laterally, for simultaneously forming receive samples along a plurality of scan lines. The wave or displacement may be monitored in one, two, or more directions.

A region of interest is monitored to detect the wave. The region of interest is any size. Since the focal region is extended using the swept focal positions, the monitoring may be over a greater depth, lateral range, area, or volume. Waves are generated along the focus. For the axially extended focus in one example, an area of 4 cm in depth and 6 mm in azimuth may be monitored. Laterally spaced locations are monitored for each depth independently. The displacements are tracked at each of a plurality of laterally spaced locations for each depth. The tracking is performed without combining the information over a range of depths. This is possible since sufficient intensity of pushing is applied over the axial extent, allowing for ARFI imaging with greater depth resolution.

For a laterally extended focus, a greater range of locations may be monitored as well. For example, the axial displacement is monitored at one or more depths for each scan line. By including a wider ARFI beam laterally, a greater number of scan lines may be monitored for axial displacement per ARFI beam. For example, eight or more (e.g., 16) scan lines are monitored for each ARFI pushing pulse.

The detection region is monitored by ultrasound. For example, B-mode scans are performed to detect tissue displacement caused by the wave. Doppler, color flow, or other ultrasound mode may be used to monitor for the shear wave.

The monitoring is performed for any number of scan lines. For example, four receive beams are formed in response to each monitoring transmission. After transmitting the excitation to generate the wave or displacement, B-mode transmissions are performed repetitively along one or more transmit scan lines and receptions are performed along corresponding receive scan lines. In other embodiments, only a single receive beam or other numbers of receive beams are formed in response to each transmission. Some of the ultrasound data, such as at the beginning or end of the repetitions, may not be responsive to the wave or displacement.

The transmission and reception for detection are performed multiple times to determine change due to displacement over time. Any transmission and reception sequence may be used. The detection of displacement may be interleaved with other scanning, such as scanning different regions for displacement separately.

The displacement is calculated from the ultrasound scan data. The tissue moves between two scans. The data of one scan is translated in one, two, or three dimensions relative to the data in the other scan. For each possible relative position, an amount of similarity is calculated for data around a location. The amount of similarity is determined with correlation, such as a cross-correlation. A minimum sum of absolute differences or other function may be used. The spatial offset with the highest or sufficient correlation indicates the amount and direction of displacement for a given location. In other embodiments, a phase offset of data received from different times is calculated. The phase offset indicates the amount of displacement. In yet other embodiments, data representing a line (e.g., axial) at different times is correlated to determine a shift for each of a plurality of depths along the line.

Displacements are determined for a given location at different times, such associated with sequential scans. The displacement is determined with respect to an initial or reference frame of scan data (i.e., cumulative displacement). Alternatively, the displacement is determined from the immediately prior frame of scan data, such assigning the previous frame as the reference on an ongoing basis (i.e., incremental displacement). The temporal profile for a given location indicates displacement caused by the wave over time.

Where the focal region extends sufficiently for the desired measurements, a single ARFI pushing pulse is used. Where a broader region of interest exists despite the time-varying focus, the acts 30-36 may be repeated. The transmissions and receptions for displacement detection are interleaved with ARFI beams to scan different regions of tissue. To monitor a larger region, acts 30-36 are repeated for other locations. For each receive beam location, a time profile of motion information (i.e., displacements) is provided. A separate time profile is provided for each axial depth and/or lateral location.

The displacement information, with or without a time profile, is used to determine a characteristic of the tissue. The characteristic is determined at each location. Any characteristic may be determined, such as an elasticity, strain, shear velocity, longitudinal wave velocity, modulus, or other viscoelastic property. The displacements themselves may be used to represent the tissue, such as the magnitude of the displacement.

In act 38, an image is generated. The image represents the tissue characteristic or property. The image is a function of the displacement. Using the displacements themselves or a characteristic derived from the displacements (e.g., shear modulus), information to be displayed is calculated. For example, a numerical or textual indication of the property may be displayed. In other embodiments, a plot and/or line fit and slope value are output. For example, displacement over time is displayed for each of one or more locations. The viscoelastic property is communicated to the user in the image. The image may be a graph, such as a plot of values as a function of location.

The image may additionally include a one, two, or three-dimensional representation of the property, displacement, or other wave information as a function of space or location. For example, the shear velocity throughout a region is displayed. Shear velocity values modulate color for pixels in a region in a gray-scale modulated B-mode image. The image may represent displacement information, such as shear or moduli (e.g., the shear moduli) for different locations. The display grid may be different from the scan grid and/or grid for which displacements are calculated. Color, brightness, luminance, hue, or other characteristic of pixels is modulated as a function of the information derived from the displacements.

In one embodiment, the image is a function of displacements from different depths. Using one, two, or three-dimensional imaging, the different locations of tissue represented in the image include different depths. For numerical or textual information, the displacements from different depths are used to derive the value or values for different depths. Due to the swept focus of the ARFI beam, displacement at different depths may be detected. The displacement for different lateral positions is detected. By extending the focus for the ARFI beams, more locations in an area or volume may be monitored and used for imaging.

In other embodiments, the displacements are used for shear wave velocity imaging. The distribution of shear velocities in a two or three-dimensional region are determined and mapped to image values. In another embodiment, shear wave velocity point quantification is performed. The value of the shear wave velocity at a location is displayed as text or a numerical value.

FIG. 12 shows one embodiment of a system 10 for swept focus in acoustic radiation force impulse scanning. Ultrasound generates tissue displacement, such as through creation of a shear or longitudinal wave, and scan data responsive to the tissue responding to the displacement is used to determine a property. The system 10 is a medical diagnostic ultrasound imaging system. In alternative embodiments, the system 10 is a personal computer, workstation, PACS station, or other arrangement at a same location or distributed over a network for real-time or post acquisition imaging.

The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted designation of a region of interest for which information is to be obtained.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing. The waveforms are generated and applied to a transducer array with a time varying focus. For example, the relative phasing varies over time during the generation of the transmit beam. The waveforms of each channel incorporate the phase variation, resulting in an ARFI pulse or beam with swept focus or multiple focal locations.

The transmit beamformer 12 includes amplifiers and phase rotators 13 each channel. The amplifiers control the amplitude of the waveforms for each channel and the corresponding beam being generated.

Each phase rotator 13 is controlled to apply a phase at a time to a generated waveform or a waveform being generated. Based on control signals, such as a buffer of phases in sequence, the phase rotator 13 is configured. Other configurations using software and/or hardware may be used. In one embodiment, the phase rotators 13 are controlled by a combination of constant, linear, and quadratic phase terms. The phase rotators 13 of the channel of the transmit beamformer 12 are configured to apply different phase profiles across the aperture of the transducer 14 over time and/or to the same ongoing waveforms. The resulting waveforms are generated by the transmit beamformer 12 for creating an ARFI pulse. The phase rotators 13 respond to changes in phase as needed to sweep the focus during a single transmit beam. The focus is shifted laterally, axially, or both, such as creating a line of focal points over time in a same transmit beam.

The transmit beamformer 12 connects with the transducer 14, such as through a transmit/receive switch. Upon transmission of acoustic waves from the transducer 14 in response to the generated waves, one or more beams are formed during a given transmit event. The beam is an ARFI pulse with a swept focus.

For scanning tissue displacement, a sequence of other transmit beams are generated to scan a one, two or three-dimensional region. Sector, Vector®, linear, or other scan formats may be used. The same region is scanned multiple times. The scanning by the transmit beamformer 12 occurs after transmission of the ARFI pulse. The same elements of the transducer 14 are used for both scanning and displacing tissue, but different elements, transducers, and/or beamformers may be used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms, and connects with the receive beamformer 16 for converting acoustic echoes into electrical signals. The transducer 14 transmits the ARFI pulse. The waveform is focused at a tissue region or location of interest in the patient. The acoustic waveform is generated in response to applying the electrical waveform to the transducer elements. The waveform causes tissue displacement, either directly or through generation of a wave (e.g., shear wave).

For scanning with ultrasound to detect displacement, the transducer 14 transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band.

The receive beamformer 16 outputs beam summed data representing spatial locations. Data for a single location, locations along a line, locations for an area, or locations for a volume are output. The data may be for different purposes. For example, different scans are performed for B-mode or tissue data than for shear wave detection. Alternatively, the B-mode data is also used to determine displacement caused by a shear wave.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information from beamformed ultrasound samples.

In one embodiment, the processor 18 includes one or more detectors and a separate processor. The separate processor is a control processor, general processor, digital signal processor, graphics processing unit, application specific integrated circuit, field programmable gate array, network, server, group of processors, data path, combinations thereof or other now known or later developed device for determining displacement and/or calculating tissue properties. For example, the separate processor performs acts 36 and 38 of FIG. 1. The processor 18 is configured by software and/or hardware to perform the acts.

In one embodiment, the processor 18 estimates tissue displacement over time as a function of the output data from the receive beamformer 16. The displacements are estimated as a profile or data representing a curve of magnitude of displacement as a function of time. The displacement profile may be obtained by correlating or otherwise determining level of similarity between reference data and data obtained to represent the tissue at a different time.

The processor 18 is configured to calculate tissue characteristics from the displacements of the tissue over time. For example, a shear velocity is calculated from the displacement over time. The amount of displacement divided by the time provides velocity. In one embodiment, the processor 18 calculates viscosity and/or modulus. The processor 18 may calculate other properties, such as strain or elasticity. In yet other embodiments, the processor 18 determines the maximum displacement or other characteristic of displacement or the displacement profile as the characteristic.

The processor 18 generates and outputs image or display values mapped from the property to the display 20. For example, the shear modulus or other value is determined. A text or numerical indication of the property is displayed to the user. A graph of the property over time may be displayed.

In one embodiment, the property is displayed as a function of location. Displacements for a limited number of locations are available in response to an ARFI pulse with a single focus. With a swept focus for the ARFI pulse, displacements for a larger number of locations and respective larger linear, area, or volume extent are available. Values, graphs, and/or tissue representations may be displayed using the displacements at different locations. By using the swept focus as compared to a single focus for the ARFI pulse, a same number of locations may be monitored with fewer ARFI pulse transmissions for quasi-real-time (e.g., 5-19 Hz) imaging. By using the swept focus as compared to a single focus for the ARFI pulse, greater spatial resolution for displacements and corresponding tissue characteristics may be provided.

For a representation of the tissue, the magnitude of the tissue characteristic modulates the color, hue, brightness, and/or other display characteristic for different pixels representing a tissue region. The processor 18 determines a pixel value (e.g., RGB) or a scalar value converted to a pixel value. The image is generated as the scalar or pixel values. The image may be output to a video processor, look-up table, color map, or directly to the display 20.

The processor 18 and the transmit beamformer 12 operate pursuant to instructions stored in the memory 22 or another memory. The instructions configure the processor 18 and/or the transmit beamformer 12 for operation by being loaded into a controller, by causing loading of a table of values (e.g., phase profile table), and/or by being executed. The transmit beamformer 12 is configured by the instructions to cause generation of an ARFI beam with a swept focus. The processor 18 is programmed for measuring tissue displacement and generating an image.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays one or more images representing the tissue characteristic or other information derived from displacements. As an example, a two-dimensional image or three-dimensional representation of displacement or tissue characteristics as a function of location is displayed. Alternatively or additionally, the image is a graph, a number, or text representation of a value or graph. For example, a shear modulus, strain, elasticity or other value or graph is displayed as the image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for swept focus in acoustic radiation force impulse scanning, the method comprising:
    transmitting, from an ultrasound transducer, a transmit beam with a time varying focal position as an acoustic radiation force impulse, the time-varying focal position having a focus in axial, azimuth, and elevation dimensions at each time to form a line focus for the transmit beam;
    tracking displacements of tissue at different depths from the ultrasound transducer, the displacement being in response to the acoustic radiation force impulse; and
    generating an image, the image being a function of the displacement of the tissue at the different depths.

2. The method of claim 1 wherein transmitting comprises transmitting the transmit beam as a single transmit beam with the time varying focal position.

3. The method of claim 1 wherein transmitting comprises generating the transmit beam with element waveforms that are continuous over time and have different amounts of phase change over the time relative to each other.

4. The method of claim 1 wherein transmitting comprises generating the transmit beam with different waveforms where phase changes by different amounts over time for the different waveforms.

5. The method of claim 1 wherein transmitting comprises generating the transmit beam with waveforms from different elements of the ultrasound transducer, each of the waveforms having a constantly changing phase term over time.

6. The method of claim 1 wherein transmitting comprises transmitting the transmit beam with element waveforms that are continuous.

7. The method of claim 6 wherein transmitting comprises transmitting with the acoustic radiation force impulse having one hundred or more cycles.

8. The method of claim 1 wherein transmitting comprises transmitting with the time varying focal position varying by axial position.

9. The method of claim 1 wherein transmitting comprises transmitting with the time varying focal position varying by lateral position.

10. The method of claim 1 wherein transmitting further comprises transmitting the transmit beam with an amplitude modulation that is time varying with the time varying focal position.

11. The method of claim 1 wherein transmitting further comprises transmitting the transmit beam with an aperture size that is time varying with the time varying focal position.

12. The method of claim 1 wherein tracking comprises tracking the displacements laterally and independently at each of the different depths.

13. The method of claim 1 wherein tracking comprises tracking the displacements axially at each of the different depths and along at least eight scan lines.

14. The method of claim 1 wherein generating comprises generating the image with pixels modulated as a function of the displacements in a two or three-dimensional field.

15. In a non-transitory computer readable storage medium having stored therein data representing instructions executable by a programmed processor for swept focus in acoustic radiation force impulse scanning, the storage medium comprising instructions for:
    altering a phase profile across an array of transducers over a time period;
    generating continuous transmit waveforms over the time period with the altering phase profile; and
    transmitting a beam of acoustic energy as an acoustic radiation force impulse from the array with the continuous transmit waveforms over the time period, the beam having a line focus in three-dimensions in response to the altering phase profile.

16. The non-transitory computer readable storage medium of claim 15 wherein altering the phase profile comprises altering an amount of phase change differently for different ones of the transducers.

17. The non-transitory computer readable storage medium of claim 15 wherein generating comprises generating the continuous transmit waveforms each as one hundred or more cycles without a gap of more than one cycle without change in amplitude of the continuous transmit waveform.

18. The non-transitory computer readable storage medium of claim 15 wherein transmitting the beam with a line focus comprises transmitting the beam with a time varying focal position, the time varying focal position changing axially, laterally, or axially and laterally.

19. A system for swept focus in acoustic radiation force impulse scanning, the system comprising:
- a transmit beamformer configured to generate waveforms for an acoustic radiation force impulse pulse with a time varying focal point in elevation, azimuth, or combinations thereof;
- a one-dimensional ultrasound transducer connected with the transmit beamformer such that the one-dimensional ultrasound transducer transmits the acoustic radiation force impulse pulse in a patient in response to the waveforms;
- a receive beamformer configured to output data representing spatial locations as a function of received acoustic signals;
- a processor configured to estimate displacement in the patient over time as a function of the output data; and
- a display operable to display an image, the image being a function of the displacement.

20. The system of claim 19 wherein the transmit beamformer comprise a phase rotator in each of a plurality of channels, the phase rotators configured to apply different phase profiles across an aperture of the one-dimensional ultrasound transducer in generating the waveforms for the acoustic radiation force impulse pulse, the acoustic radiation force impulse pulse being a single transmission.

* * * * *